United States Patent [19]

Saxon et al.

[11] Patent Number: 4,927,765

[45] Date of Patent: May 22, 1990

[54] AUTOMATIC REAGENT DISPENSER

[75] Inventors: Ronald L. Saxon, Port Murray; Leroy Zeger, Passaic; Kenneth Horbatt, Pompton Plains, all of N.J.

[73] Assignee: Pharmacia ENI Diagnostics, Inc., Fairfield, N.J.

[21] Appl. No.: 162,172

[22] Filed: Feb. 29, 1988

[51] Int. Cl.$^5$ .......................................... G01N 35/00
[52] U.S. Cl. ....................................... 436/43; 436/49; 422/63; 422/100; 73/864.14; 141/1; 141/27; 141/130
[58] Field of Search ................................ 436/43–49; 422/63–67, 100; 141/1, 26, 27, 130; 73/864.01, 864.14, 864.16; 222/567

[56] References Cited

U.S. PATENT DOCUMENTS

| | | | |
|---|---|---|---|
| 3,489,525 | 1/1970 | Natelson | 422/67 |
| 3,817,425 | 6/1974 | Liston . | |
| 3,873,274 | 3/1975 | Neisius | 422/75 |
| 3,881,527 | 5/1975 | Shapiro | 141/24 |
| 4,088,446 | 5/1978 | Huber et al. | 422/100 |
| 4,277,440 | 7/1981 | Jessop . | |
| 4,318,884 | 3/1982 | Suzuki | 422/63 |
| 4,436,631 | 3/1984 | Graham, Jr. et al. | 210/772 |
| 4,452,899 | 5/1984 | Alston . | |
| 4,678,752 | 7/1987 | Thorne et al. . | |
| 4,785,677 | 11/1988 | Higo | 73/864.14 |

OTHER PUBLICATIONS

"Practical Chemistry Automation for Small Hospital and Satellite Testing Laboratories", American Clinical Products Review, Dec., 1986, pp. 42–45.

Operating Instructions for "Selectapette Pipette System", Clay Adams, Sept. 6, 1974, pp. 1–2.

Brochure for Tecan "Sampler 500", Tecan AG and Tecan U.S., Ltd., undated, pp. 1–6.

Primary Examiner—Michael S. Marcus
Assistant Examiner—D. John Griffith, Jr.
Attorney, Agent, or Firm—Davis Hoxie Faithful & Hapgood

[57] ABSTRACT

Method and apparatus for automatically pipetting reagents which avoid contamination of the reagents. The reagents are withdrawn from a reagent bottle via a pipette tip which is unique to a particular reagent. The pipette tip is moved to a cuvette where the reagent is dispensed and then returned to rest in the cap of the reagent bottle. The apparatus for carrying out the method includes a pump, pipette pick-up device, reagent bottle cap and bottle rack.

6 Claims, 3 Drawing Sheets

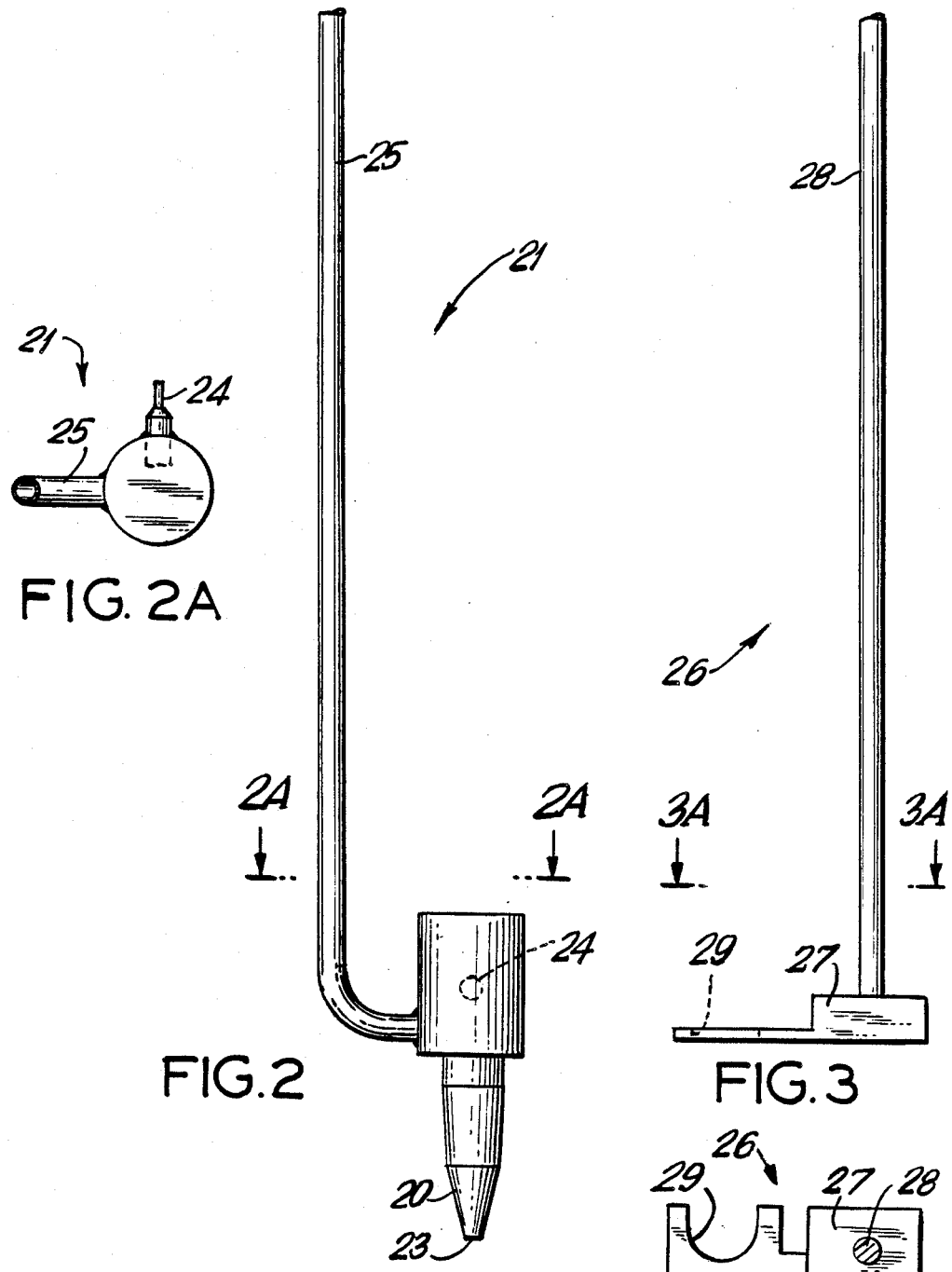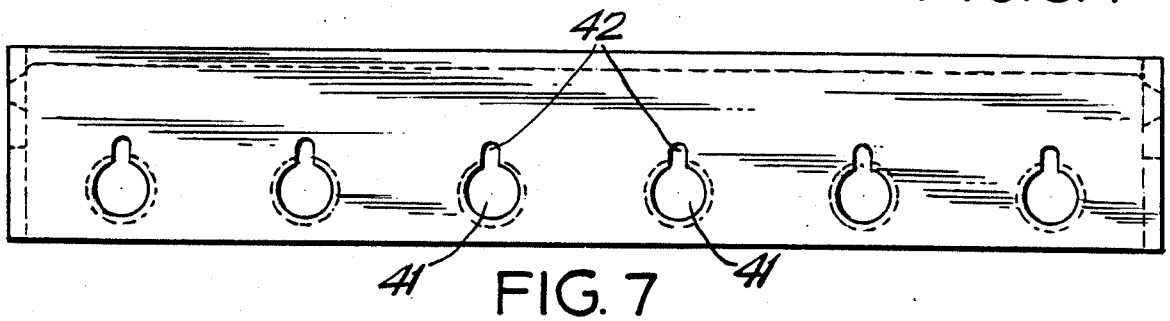

AUTOMATIC REAGENT DISPENSER

FIELD OF THE INVENTION

The invention relates to an automated pipetting system.

BACKGROUND OF THE INVENTION

Automated pipetting systems wherein small volumes from a number of reagents are pipetted into one or more cuvettes are known in the prior art. Applicants have made improvements in a number of components used in prior systems and have thus invented an improved apparatus for and an improved method of automatically pipetting reagents. Individual components thus improved are the aspirating pump, the device for picking up tips, the cap for bottles of reagents used in the procedure and the rack for holding those bottles. These improvements allow for an improved method of dispensing reagents which avoids cross-contamination of reagents and the cuvettes being loaded.

Pump

Prior to this invention, syringe pumps were used to aspirate and dispense biomedical reagents. These are positive displacement pumps in which the piston is sealed to the cylinder by an interference seal. (They are called syringe pumps because of the use of glass hypodermic syringes as pumps.) In a typical application, the pump was filled with a working fluid which displaced the air in the pump and filled the associated tubing connecting the pump to the pipette tip and the pipette tip itself. The pump piston was therefore hydraulically coupled to the fluid to be aspirated.

The interference seal in the pump and the necessity to accelerate and move all of the working fluid required relatively high forces to move the pump piston in the pump bore. The hydraulic coupling of the working fluid to the aspirated fluid involved the possibilities of contamination and/or dilution of the aspirated fluid with working fluid. The maintenance of the hydraulic coupling required that the working tip be permanently coupled to the pump and primed with working fluid or, if a replaceable working tip were used, that a priming cycle be included to prime each replaceable tip.

Where permanent tips were used, the potential existed for cross-contamination of different fluids aspirated in the common tip, either through the working fluid or through adsorption of aspirated fluid on the inside or outside of the working tip. To supply working fluid for flushing the working tip and/or priming, a source of working fluid and a provision for waste was required. In some applications, the waste material would be hazardously contaminated. To direct the working fluid to the pump, a valve was required.

Tip Pick-Up Device

Prior to this invention, disposable pipette tips were picked up by the pipetter either manually or by automatic clamping by some type of articulated mechanism which clamped onto either the inside or outside diameter of the tip. The disadvantage of manual assembly is that it does not allow for automated pipetting.

The articulated mechanisms also have their disadvantages: the clamp and its actuator had to be carried with the tip, the clamping action was usually a motion different from the articulation that engages the pipette tip on the pipetter, and the acceptance tolerance of the clamp was small.

Reagent Bottle Cap

Prior to this invention, biomedical reagents were aspirated directly from reagent bottles. The reagent bottles were capped with an elastomeric stopper and sealed with a metallic cap. To aspirate fluid the metallic cap had to be destroyed and the elastomeric stopper removed. Aspiration could then be performed through the open mouth of the bottle by manual or automatic operations.

During the aspiration cycle the liquid in the bottle was open to the atmosphere and was free to evaporate. For manual operations, a stopper had to be replaced in the bottle mouth to retard evaporation between aspirations or during storage. For automatic operations, the liquid was open to the atmosphere as long as the bottle was in place in the automatic pipetting device. A stopper had to be replaced in the bottle mouth to retard evaporation during storage.

During the insertion of the aspirator tip into the bottle, alignment and penetration of the tip was controlled manually if the aspiration operation was manual. Alignment and penetration of the tip was controlled by the geometry of the aspiration device if the aspiration operation was automatic.

Two of the disadvantages of these prior art bottle caps are that first, the reagent in the bottle is able to evaporate during the aspiration procedure or storage, and second, the alignment of the tip in the bottle was manually controlled, or, for automatic pipetters, alignment was accomplished with permanent (non-disposable) tips which were mechanically aligned with the bottle.

Bottle Rack

Racks which supported and located the bottoms of the bottles are known in the prior art. These racks were generally not adaptable for use in automatic pipetting from the bottle using disposable pipette tips which are stored in the bottle. Furthermore, racks which merely orient the bottom of the bottle do not provide positive retention of the bottles during transport to and from a storage location.

SUMMARY

The invention comprises apparatus for and a method of pipetting reagents and loading them into cuvettes which avoids cross-contamination of the reagents. This is accomplished by moving an aspirating arm in the X, Y and Z axes to a selected reagent bottle, engaging a pipette tip located in the cap of the reagent bottle, aspirating reagent, moving the tip out of the reagent bottle and, without passing over any other reagent bottles or non-selected cuvettes, into a selected cuvette and ejecting reagent into that cuvette. The pipette tip is then returned to the cap of the bottle before the aspirating arm moves to the next reagent. The process is repeated, loading various different reagents into the same cuvette, or one or more reagents into a series of cuvettes.

Aspiration is performed by using a linear displacement piston cylinder which is actuated by a stepper motor. A small, predictable leakage between piston and cylinder permits use of a small motor but does not cause inaccurate measurement or dripping of aspirated reagents. An aspirating arm supports a tip pick-up assembly and moves it to and from the various aspirating and loading stations of the device. The pick-up tip of this assembly forms a self-locking taper when it is inserted into a pipette tip.

To eliminate contamination between reagents, separate pipette tips are used for each reagent. Each reagent bottle is provided with a cap especially designed to hold such a pipette tip. The cap includes a sleeve to guide the pipette tip into the reagent bottle for aspiration of reagent. The cap also includes a flange which fits into a slot in a reagent bottle rack so that the bottle is maintained in the correct orientation. The rack tilts the bottle so that the pipette tip is directed to the lower side of the bottom of the bottle.

DESCRIPTION OF THE DRAWINGS

FIG. 2 is a side view of the pipette tip pick-up assembly;

FIG. 2A is a plan view from line 2A showing the pipette tip-pick-up assembly;

FIG. 3 is a side view of the pipette tip ejector mechanism;

FIG. 3A is a plan view from line 3A showing the arm and slot;

FIG. 7 is a plan view of the bottle rack top.

DETAILED DESCRIPTION

Figure 1:
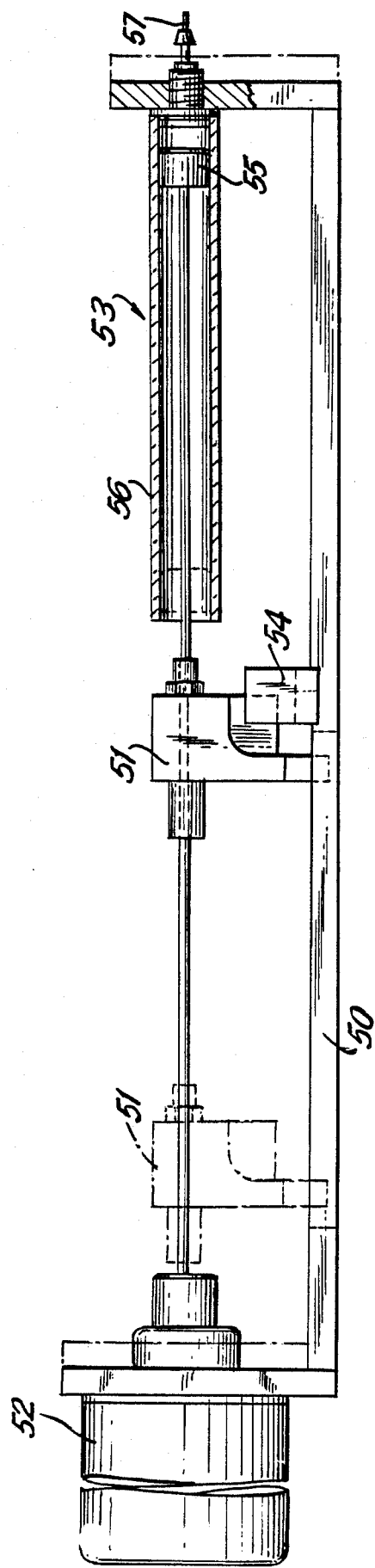
FIG. 1 is a longitudinal section of the pump piston and its motor.

The invention includes a low friction air column fluid aspirator shown in FIG. 1. This aspirator consists of four basic components, the frame 50, the guide 51, the actuator 52 and the cylinder 53. The actuator and the cylinder are arranged at and fastened to opposite ends of the frame so that the longitudinal axes of the actuator and the cylinder are collinear. The end of the actuator is attached to the end of the cylinder using the guide. The guide prevents the actuator from rotating, it maintains the actuator and the cylinder shafts in the collinear position, and it acts as a flag for triggering a position sensitive sensor 54, preferably an optical sensor, which provides an indication of home position.

The linear actuator is preferably a linear stepper motor capable of providing a force over distance sufficiently large to fully actuate the cylinder. In other embodiments of the invention, the linear actuation may be provided by a device capable of providing a force over distance, and capable of having the acceleration and speed of the linear motion be controlled at the command of an external electronic controller or be mechanically preset. Such devices may include but are not limited to a motor/gear/rack assembly, a rotary motor and crank arm, or a motor driven cam.

The cylinder preferably consists of a carbon and graphite piston 55 connected to a shaft using an angularly articulated joint which slides inside a glass tube 56. One end of the glass tube is open; the shaft protrudes through the opening. The other end of the glass tube is sealed closed in such a manner that a connective tube 57 may be attached to the cylinder so that it communicates with the chamber inside the glass tube. The connective tube is capable of conducting air pressure and volume to a remote location.

The diameter of the piston and the glass tube are carefully controlled. The outside diameter of the piston is smaller than the inside diameter of the glass tube by a small amount such that the piston essentially rides on a layer of air between the piston and the cylinder wall. In a preferred embodiment of the invention the leakage between the piston and the cylinder is on the order of one percent of the swept volume of the pump. The sealing of the pump piston to the pump bore (glass tube 56) is a clearance fit precisely controlled to reduce the leakage between the piston and the bore to a very low amount. The coupling of the pump piston to the aspirated fluid is through an air column.

The clearance fit between the piston and the bore of the pump produces a small, predictable amount of leakage. This leakage reduces the required actuation force to a very small amount, allowing the use of a small low power motor. The low leakage in the pump is not significant to system performance since the pumping pressures are small and the pumping duration is short. The leakage losses are insignificant compared to the volume being pumped. Each machine needs to be calibrated once to account for the low leakage rate.

The electronic circuitry which drives this version of the invention is pre-programmed to receive a signal from the home sensor 54 and a signal to start the dispense cycle. After receiving the start signal, a specific actuation sequence is followed to assure accurate dispensing and the ability to transport the aspirated fluid without losing any portion of the fluid.

The sequence essentially is to fill the cylinder with air, engage a working pipette tip, flush out any fluid accumulated in the tip, aspirate a small amount of air to later be used in flushing the tip, insert the working pipette tip into the fluid to be pipetted, aspirate a controlled quantity of fluid, remove the working pipette tip from the fluid, aspirate a small amount of air to serve as a transport cushion, move the working pipette tip and aspirated fluid to a desired dispense location, dispense the fluid and flush the tip with the excess air previously aspirated.

In another embodiment of the invention, an algorithm may be included in the aspiration protocol to accommodate variation in fluid density. For example, one can convert the gravimetric component of the aspiration to a purely volumetric aspiration to assure accurate and density.

The air coupling between the pump piston and the aspirated fluid eliminates the need for a working fluid, a supply source of the working fluid, a waste disposal system for the working fluid and a technique for directing and dispensing the working fluid and the valves, valve actuators, connective tubing and decision making devices associated therewith. The air coupling also allows the convenient use of disposable pipette tips which may be inexpensively dedicated to individual aspirated fluids. The potential for cross-contamination of the aspirated fluid is virtually eliminated and the need for priming the tip prior to using the pump is eliminated. Dissolution of the aspirated fluid with working fluid is also eliminated. The nature of the piston and cylinder materials provides that the start-up force for the pump is the same every time regardless of how long the system has been idle or how long it has been running.

Three motors serve to move the aspirating arm in the X, Y and Z axes as the aspirating arm moves through the dispensing procedure. The motor that moves the arm in the Z axis also provides the power for ejecting the pipette tip. As mentioned previously, a low power motor serves to provide the power for the aspiration and the ejection of the reagents. The aspirating arm comprises at its distal end a pipette tip engagement mechanism, shown in FIGS. 2, 2A, 3 and 3A.

The pipette tip engagement mechanism includes a ported, multi-angled conical pick-up tip 20 affixed to the end of a linear articulated mechanism 21, and an ejector mechanism 26 (shown in FIGS. 3 and 3A), affixed nearby the articulated mechanism, able to travel with it, and articulated so as to be able to surround the conical tip to present a barrier to the free return movement of the pipette tip and the pick-up tip.

The port 23 in the pick-up tip is sufficiently large to pass an air volume to aspirate the required amount of fluid into the pipette tip within the time allocated for the operation. In one embodiment of the invention shown in FIG. 2, the port is central to the pick-up tip and coincident with its axis. In another embodiment of the invention, one which allows a greater acceptance tolerance of the pipetting mechanism, the port is a cross-hole which connects with a central port which stops short of the extreme end of the pick-up tip. By this means, the extreme end of the pick-up tip is allowed to be smaller in diameter, and in the extreme is a sharp point, which allows a radial positional error of up to 100% of the radius of the pipette tip entrance.

The extreme end of the pick-up tip is a conical angle greater than the self-locking taper required for holding the pipette tip and is sufficiently large to accommodate the difference in diameters between the extreme end of the pick-up tip and the nominal locking diameter of the pick-up tip consistent with maximizing the linear travel of the pick-up tip. In the minimum extreme, the angle is the same as the holding taper and in the maximum extreme the angle is 45 degrees.

The pick-up tip is affixed to the end of a linear actuator with sufficient travel to engage the pipette tip under all conditions of vertical positional tolerances and to perform the locking action. Normally, this travel is significantly less than the travel required to otherwise transport the pipette tip within the pipetter system.

A tube 25 (which is metallic in a preferred embodiment of the invention) is attached to connective tube 57. Tube 25 conducts the air volume from port 23 to cylinder 53 of the aspirator. Flag 24, shown in FIG. 2A, on tube 25 provides positional information to a control circuit (not shown).

In a preferred embodiment of the invention, the ejector mechanism 26, shown in FIGS. 3 and 3A, consists of an arm 27 affixed to a shaft 28, parallel to the pick-up tip linear actuation axis, which is in turn affixed to an actuator capable of rotating the shaft. In other embodiments of the invention, the arm may be actuated with a translational actuator or with another form of rotational actuator with its axis other than parallel to the pick-up tip linear actuation axis.

The ejector arm incorporates a slot 29 shown in FIG. 3A, with a semi-circular bottom, adapted to clear the outer diameter of the pick-up tip at all conditions of positional tolerance while being simultaneously small enough to interfere with the outside diameter of the engagement end of the pipette tip. By the means of rotating the ejector shaft 28, the ejector arm 27 surrounds the pick-up tip. The pick-up tip linear actuator is then actuated in a direction opposite that required to engage the pipette tip thereby forcing the pipette tip off of the locking taper. This operation is intended to be performed over the reagent bottle cap, thus depositing the tip in the chute of the cap.

The pipette tip engagement mechanism automates the insertion and the ejection of a pipette tip on a pipetter. The mechanism allows insertion of the pick-up tip into the pipette tip over a wide range of radial and angular positions, seals the pipette tip to the pick-up tip, and provides for the ejection of the pipette tip after that tip has been used for aspirating and dispensing reagent.

The advantages of this pipette tip engagement mechanism are that the configuration of the pick-up tip will accommodate a positional error relative to the coincident vertical axes of the pipette tip and pick-up tip in any radial direction from the vertical axis of the pipette tip of 70% to 90% of the inside radius of the entrance of the pipette.

The configuration of the pick-up tip will accommodate an angular error relative to the vertical axes of the pipette tip and pick-up tip which is a mathematical function of the elliptical distortion allowed in the pipette tip by its design.

The configuration of the pick-up tip seals the pipette tip to the pick-up tip by distortion of a seal provided within the pipette tip entrance for that purpose. This distortion is accomplished by pushing the pick-up tip into the pipette tip. The action of pushing the pick-up tip into the pipette tip accommodates the relative diametrical tolerance of the pick-up tip and the pipette tip, the radial positional tolerance and the angular positional tolerance.

The conical configuration of the pick-up tip is such that the angle formed between the pick-up tip and the pipette tip is a self locking taper, that is, one in which the elastic wedging action which tends to release the lock is less than the frictional forces between the mating parts. This technique provides holding power which allows transportation of the pipette tip to a remote location by a pipette mechanism.

The nature of the conical configuration is such that the elastic wedging action tending to release the lock assures that the release force is less than the engagement force. The ejection of the pipette tip from the pick-up tip is therefore accommodated by mechanically interposing a barrier to the free return motion of the pipette tip. The same mechanical device which was used to engage the pipette tip is therefore used to release the pipette tip from the pick-up tip.

Figure 4:
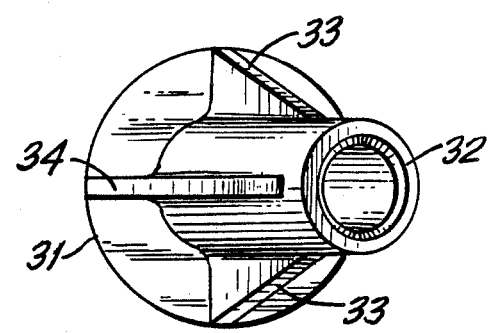
FIG. 4 is a cross-section of a reagent bottle cap adapted for use in the invention.
Figure 5:
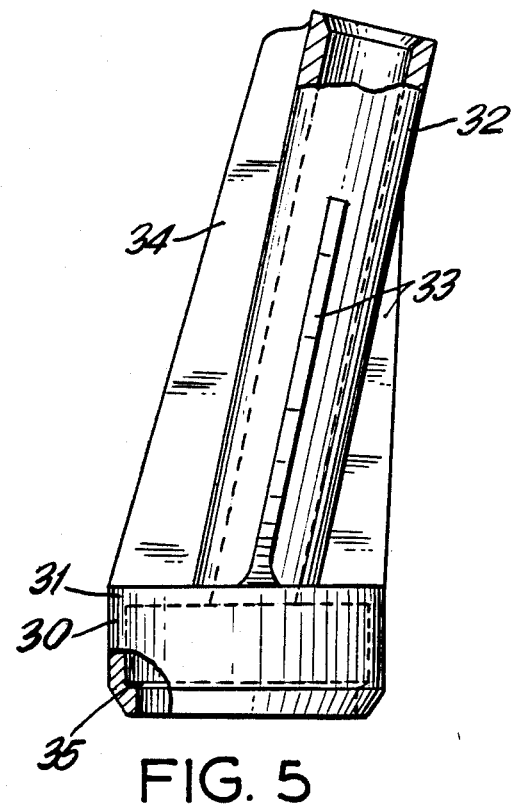
FIG. 5 is a longitudinal section of a reagent bottle cap adapted for use in the invention.
Figure 6:
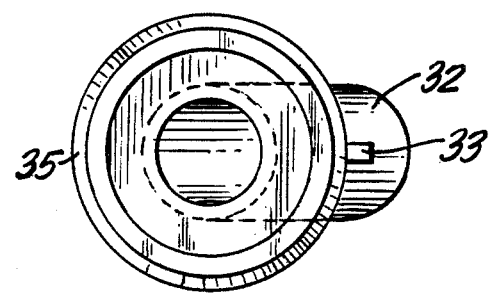
FIG. 6 is a cross-section of a reagent bottle cap adopted for use in the invention.

Each pipette tip is associated with and is returned to a particular reagent bottle. The present invention comprises a reagent bottle closure which supports such a pipette tip. This bottle closure, shown in FIGS. 4, 5 and 6 consists of two components: a cap, shown in FIGS. 4, 5 and 6 and an auxiliary stopper.

The cap is an elastomeric device comprising a cylindrical sleeve 30, a circular disc 31, a cylindrical chute 32 and a set of ribs 33, one of which is enlarged to form a fin 34. The cylindrical sleeve 30 is capable of stretching over and subsequently enclosing and interlocking with the neck of a reagent bottle. The neck of the reagent bottle has a lip at its top, and cylindrical sleeve 30 includes a conic section 35 which performs the interlocking feature by remaining in contact with the underside of the lip and the neck of the reagent bottle, so as to maintain a force on them. This is by virtue of the elasticity of the material from which the cylindrical sleeve 30 is fabricated.

The circular disc 31 is contiguous with the sleeve 30. It contacts the top of the bottle and is maintained in intimate contact with the top of the bottle by the conic section 35 of the cylindrical sleeve 30 whereby a seal is formed.

The cylindrical chute 32 is contiguous with the disc 31 and penetrates it. It is oriented to the disc so as to be able to present a pipette tip to an automatic pipetter in the proper orientation. It is long enough to support a pipette tip in close proximity to the inside bottom of the serum bottle without touching the bottom.

The set of ribs 3 is contiguous with the cylindrical chute 32 and the circular disc 31. The ribs act to maintain the chute in its proper orientation and to support it during the tip pickup operation. One of the ribs is enlarged to form a fin 34 which provides a key which fits into a slot on the rack (shown in FIG. 7) holding the reagent bottles. This key and slot arrangement prevents rotation of the cap with respect to its holder.

The auxiliary stopper (not shown) is provided to seal the cap when the life of the disposable tip is exhausted and the cap and bottle are to be stored without the tip installed. The auxiliary stopper is intended to be used for the storage period between one working day and the next.

The bottle closure provides a snap-on closure for reagent bottles which, after removal of a disposable metallic seal and the auxiliary stopper, provides several functions. First, it is a holder for a disposable pipette tip which allows one to dispense fluid from the bottle without having to wash a permanent tip and without having to dispose of a pipette tip after every use. The cap also provides a specific geometric relationship between the disposable tip and the reagent bottle which facilitates the pickup of the tip by an automatic dispenser device and minimizes the unusable residual volume in the bottle.

Furthermore, the closure provides a sealing cap for the reagent bottle which retards evaporation of the reagent during the aspiration procedure, during a work period and during storage. It further provides a retention system which restrains the cap from changing its orientation in its rack and thereby its orientation to the automated dispenser device. It interlocks with the rack so as to inhibit the bottle and cap from falling out of the rack during transportation. Such transportation may be from a loading station to the automated dispenser device or to any other station such as a refrigerated storage location.

The reagent bottles are tilted so that the pipette tip is always oriented to be at the side of the bottle which is lowest. The tilt, which is about 10° to 15° in a preferred embodiment of the invention, is provided by the rack in which the reagent bottles rest. The rack includes a base, uprights and a top. The base of the rack is configured to fit into a pipetting mechanism in a way that limits the movement of the rack, in any direction, to an amount less than the total acceptance tolerance of the pipetting mechanism tip and pipette.

The base contains cylindrical wells which receive reagent bottles. The depth of the wells is less than the maximum amount that the bottle and cap assemblies can be raised in the rack; that maximum dimension is limited by the configuration of the bottle cap.

On each side of the rack there is a vertical upright which supports the top of the rack at the proper distance above the base to accept the bottles in the wells and engage the top of the bottle caps. The upright provides a convenient handle for removal of the racks from the pipetting machine.

The top of the rack shown in FIG. 7, is horizontal and parallel to the base. The top is pierced with as many extended holes 41 as there are wells in the base. The holes are positioned laterally coincident with the centerlines of the wells and are orthogonally offset so as to accommodate any angular relationship between the top of the bottles and the top of the caps. The holes are larger than the tops of the caps.

The holes include an extension which in a preferred embodiment of the invention is a slot 42, approximately 25% of the diameter of the hole in width projecting radially away from the slot towards the rear. This slot 42 accepts the fin 34 from a bottle cap so as to limit the rotation of the cap with respect to the rack.

The caps are normally perpendicular to the top of the rack in the lateral direction and oblique to the top of the rack in the distal direction. The holes in the rack therefore allow ready insertion of the cap from the direction 180° opposed to the oblique angle. In another embodiment of the invention, the oblique angle of the cap relative to the top of the rack is in the same direction as the direction of insertion. In this embodiment the release in the top of the rack is not required.

This bottle rack provides orientation of reagent bottles relative to an automatic pipetting system to assure reliable pickup of pipette tips which are stored in the bottles. It also provides retention of the reagent bottles during transportation. The configuration of the rack provides a locational device in the form of an extension which maintains entrance of the pipette tip in a predictable location.

The configuration of the rack includes a keying slot which interlocks with the bottle cap so as to prevent rotation of the bottle cap with respect to the rack and loss of angular orientation.

The steps of the one embodiment of the method of the invention are set forth in the following example.

EXAMPLE

The aspirating arm begins at a home or start position. Before engaging a pipette tip, air is aspirated by displacing the piston to its maximum stroke. Even for the maximum stroke, the piston does not quite come all the way to the end of the cylinder. This prevents jamming of the mechanism. The pipette is moved in the X and Y axes to a preselected reagent bottle. At the reagent bottle, a tip pick-up device at the end of the aspirating arm engages a pipette tip found in the reagent bottle cap. Then, by motion in the Z axis, the arm elevates the tip clear of the reagent bottle. All air is expelled out of the aspirating arm and tip by pushing out trapped liquid in the tip. The maximum piston acceleration for maximum fluid/liquid velocity creates maximum shear at the end of the tip. Then air is aspirated. This air is used later for tip sweeping, that is, the blowing of air through the tip to sweep bubbles and pendant drops of reagent from the tip.

The pipette tip is inserted a fixed distance into the reagent bottle. A pre-selected volume of reagent is aspirated from the bottle. Motion in the Z axis elevates the pipette tip clear of the reagent in the bottle. Then, a small air slug is aspirated. This slug of air at the very end of the tip is used as a cushion to prevent dripping of the aspirated reagent during transportation to the cuvette. Motion in the Z axis elevates the tip to clear the bottle and the cap.

The pipette tip is moved to a position over a preselected cuvette by motion in the X and Y axes. The route along the X and Y axes is such that the tip never passes over another reagent bottle or a non-selected cuvette. This prevents cross-contamination of reagents during the procedure. The tip is inserted into the cuvette and the reagent is expelled into the cuvette. The piston is moved a full stroke to sweep bubbles and pendant drops of reagent from the tip. The tip is repositioned by motion in the X, Y and Z axes to the original bottle and the pipette tip is stripped off the tip pick-up device and replaced into the cap of its original reagent bottle. The aspirating arm is then moved in the X and Y axes to the next reagent bottle or to the home position as required.

What is claimed is:

1. A method for automatically dispensing one or more reagents into one or more cuvettes which avoids contamination of said reagents comprising the steps of:
   (1) moving an aspirating arm to a selected reagent bottle,
   (2) engaging a pipette tip which is supported by the cap of the reagent bottle,
   (3) aspirating a preselected volume of reagent,
   (4) elevating the aspirating arm so that the tip is clear of the bottle and its cap,
   (5) moving the aspirating arm to a selected cuvette so that the tip does not pass over another reagent bottle or a non-selected cuvette,
   (6) expelling the aspirated reagent into the cuvette,
   (7) moving the aspirating arm so that the tip is repositioned over the original bottle,
   (8) releasing the tip into the cap of the bottle and
   (9) moving the aspirating arm to the next reagent bottle.

2. The method of claim 1, further comprising the steps of elevating the pipette tip above the level of reagent remaining in the bottle and aspirating air after the preselected volume of reagent is aspirated from the bottle.

3. The method of claim 1, further comprising the steps of aspirating air before moving the aspirating arm to the selected reagent bottle and expelling that air and any liquid trapped in the tip after the tip has been engaged.

4. The method of claim 3, further comprising the step of elevating the tip clear of the reagent bottle after the tip has been engaged and before air and trapped liquid are expelled from the tip.

5. The method of claim 1, further comprising the step of aspirating air before inserting the tip a fixed distance into the bottle to aspirate reagent.

6. The method of claim 1, further comprising the step of inserting the tip into the cuvette before expelling reagent into the cuvette.

* * * * *